Figure 1:
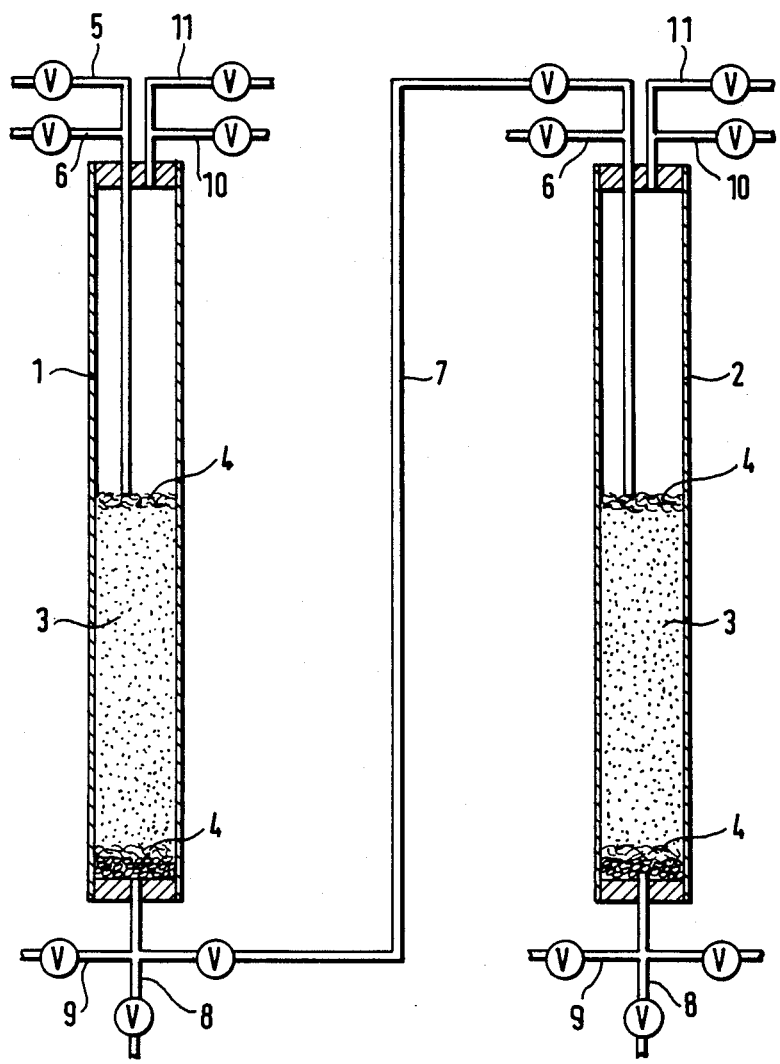

United States Patent [19]

Margureanu et al.

[11] Patent Number: 4,855,494
[45] Date of Patent: Aug. 8, 1989

[54] PROCESS FOR PRODUCING CITRIC ACID

[75] Inventors: Gabriella Margureanu, Weinheim; Friedrich Gutmann, Walldorf, both of Fed. Rep. of Germany

[73] Assignee: Joh. A. Benckiser GmbH, Ludwigshafen, Fed. Rep. of Germany

[21] Appl. No.: 697,350

[22] Filed: Feb. 1, 1985

[30] Foreign Application Priority Data

Feb. 3, 1984 [DE] Fed. Rep. of Germany ....... 3403748

[51] Int. Cl.$^4$ ............................................ C07C 51/42
[52] U.S. Cl. ................................ 562/580; 562/584; 435/144
[58] Field of Search ................. 562/580, 584; 435/144

[56] References Cited

U.S. PATENT DOCUMENTS 2,974,178  3/1961  Hwa et al. ........................... 560/218

FOREIGN PATENT DOCUMENTS 251760  1/1963  Australia ............................. 562/580
53-101303  9/1978  Japan .

OTHER PUBLICATIONS

Walch et al, Chemical Abstracts, vol. 85, No. 19043t, (1976).
Borak et al, Chemical Abstracts, vol. 84, No. 29190g (1976).
Kirk-Othmer "Encyclopedia of Chemical Technology", 3rd ed, vol. 6, pp. 16-159.

Primary Examiner—Bruce D. Gray
Attorney, Agent, or Firm—Weiser & Stapler

[57] ABSTRACT

A process for producing citric acid or other suitable acids and/or their salts from fermentation solutions. The process comprises removing high molecular weight impurities by means of membrane filtration and/or addition adsorption on a nonionic adsorption resin and removing low molecular weight impurities by anion and cation exchange and/or precipitating a citric acid as a calcium salt.

24 Claims, 1 Drawing Sheet

U.S. Patent   Aug. 8, 1989   4,855,494

PROCESS FOR PRODUCING CITRIC ACID

The present invention relates to a new process for producing citric acid or other suitable acids and/or their salts from fermentation solutions.

Citric acid is used, e.g., as a dietary acid and complexing agent in the food industry, for metal cleaning, in the pharmaceutical industry, and in many other areas.

Citric acid is produced currently mainly by fermentation with *Aspergillus niger* from sugar solutions or molasses according to older surface methods or more modern submerged methods.

Depending on the nature of the starting product used—beet sugar molasses, cane sugar molasses, starch, etc.,—and of the method used, a pretreatment must be carried out, e.g., with soluble hexacyanoferrate salts, and a number of nutrient salts with possibly needed trace elements (magnesium, zinc, etc.) must be supplied.

Depending on the starting sugar concentration and on the nature of the method used, citric acid-containing solutions are thus obtained, which contain 10-20% other organic and inorganic substances besides ca. 10 to 30% citric acid after separation of the microorganisms. These by-products originate partly from the original molasses solution, partly from the nutrient salts added to the nutrient solution and not consumed by the microorganisms, and partly as excretion products other than citric acid produced by *Aspergillus niger* during the fermentation.

The citric acid is usually precipitated for purification as the sparingly soluble calcium salt, and the citric acid is released from the calcium citrate by adding sulfuric acid. The citric acid can then be obtained from this solution in crystalline form by subsequent concentration.

In order to produce citric acid of the purity required for foods and especially for pharmaceutical purposes, it is, however, necessary to carry out this process in a much more complicated and more expensive fashion in order to separate impurities as completely as possible in every individual phase of the process. Details in this connection are explained, for example, in *Ullman's Enzyklopadie der technischen Chemie* [Ullman's Encyclopedia of Chemical Technology], 3rd edition, Volume 5, pp. 603–609 and 4th edition, Volume 9, pp. 631–633, as well as *Kirk-Othmer's Encyclopedia of Chemical Technology*, 1st edition, Volume 4, pp. 15–17, and 2nd edition, Volume 5, pp. 529–531. Some steps shall be mentioned here.

The oxalic acid which may be present as a by-product is precipitated in acidic solution with a small quantity of calcium hydroxide before the actual precipitation of the calcium citrate salt. It is only after the separation of oxalic acid that the calcium citrate is precipitated in crystalline form at a temperature of 80°–95° C. by mixing it with a small excess of calcium hydroxide while stirring. The calcium hydroxide used must therefore be as pure as possible, because contamination with magnesium, iron, and aluminum or phosphates considerably interfere with the subsequent isolation of the pure acid. The calcium citrate obtained is filtered and washed while hot in order to keep losses as low as possible, because it has an especially low solubility at 80°–95° C.

The calcium citrate thus obtained is reacted with a small excess of dilute sulfuric acid in large impeller type mixers. The calcium sulfate precipitated is filtered off. The brown filtrate is called crude acid in practice. This crude acid is subsequently decolorized, e.g., with activated carbon. The carbon with the colored impurities adhering to it is removed by filtration. The clear citric acid solution is concentrated by evaporation after ion exchange treatment, the concentrate is crystallized in several steps under vacuum or under normal pressure. Depending on the purity, the crude crystals must subsequently be subjected to one or more recrystallization steps with purification with activated carbon before chemically pure citric acid is obtained. Anhydrous citric acid is obtained by crystallization above the transition point of 36.6° C., while the citric acid crystallizes as the monohydrate under this temperature.

Besides this conventional precipitation method, other methods have also been described in some patent specifications, according to which the citric acid is produced by extraction with organic solvents. Butyl alcohol, acetone, and tributyl phosphate shall be mentioned. Since the crystallization is very difficult because of the impurities not completely removed, and the yield is unsatisfactory, these processes, elegant per se, have not found practical application so far due to being uneconomical. Extraction with certain amines was described recently.

It is the task of the present invention to obtain citric acid or other suitable acids and/or their salts from fermentation solutions in a simpler and more economical manner by separation of the impurities by special physical-chemical separation methods.

Another task of the present invention is to substantially reduce the water pollution caused by citric acid production due to substances originating from the raw materials or from the process by purposeful recovery of the said substances.

One principal task of the present invention is also to reduce the amount of other by-products generated or to eliminate such by-products altogether in the citric acid production by practically complete abandonment of the auxiliary chemicals $Ca(OH)_2$ and $H_2SO_4$, because the utilization of such by-products is increasingly problematic. The process becomes more economical hereby at the same time. FIG. 1 shows an apparatus suitable for using the process of the invention.

The solution of these tasks, which is described by the characteristics specified in more detail in the claims, is based upon the separation of the higher-molecular-weight impurities by membrane filtration, preferably ultrafiltration, or reversed osmosis, and subsequent adsorption on nonionic adsorbent resins with large specific surface and on the separation of the low-molecular-weight, especially inorganic, ions by means of cation and anion exchange resins. The citric acid solution thus purified can be crystallized directly, or, as before, be obtained after precipitation in the form of calcium citrate. The steps of membrane filtration, color adsorption on adsorbant resin and exchange of the interfering cations and anions on ion exchange resins are carried out consecutively or in another suitable order, and the individual steps can also be repeated.

The membrane filtration is a known method. For example, hollow fiber bundles are assembled as modules for industrial applications, and are used as batteries in columns in order to handle large amounts of liquid. Depending on the pore size of the membrane higher-molecular-weight compounds in the concentrate are thus separated from the low-molecular-weight compounds in the permeate. However, this method was inapplicable to the purification of citric acid solutions, because even though the membranes known hitherto do separate molecules with molecular weights above 1,000, they are unstable at low pH values of 1.5–2.2. Now, membrane materials have become known which withstand such pH values over rather long periods of time even at this separation capacity, are sufficiently permeable at low energy consumption, and can readily be cleaned.

However, not even these membranes are able to separate a large portion of the disturbing impurities from the fermentation solution, i.e., those with molecular weights of ca. 200–1,000.

The adsorptive purification of aqueous and organic solutions is a method known for a long time already. Organic components are adsorbed and enriched in this process on solids with large active surface, such as activated carbon, alumina, or silicates. The adsorbed substances can be eliminated by separation of the adsorbent-adsorbate system according to the known "solid-liquid separation" methods. In most cases, the adsorbent must be regenerated in a subsequent process step. Such purification methods have, however, only rarely been used before for mixed systems with high organic burden because of the great variety of the dissolved impurities, the differences in their adsorbability, and last but not least for economic reasons.

Another process has become known from the West German Patent Specification No. 1,274,128, according to which strongly heteropolar molecules can be separated from aqueous solutions or dispersions by means of nonionic, water-insoluble, crosslinked polymers of macroreticular structure. The adsorbents consist of polymers which are built up of ca. 2–100% vinyl benzene, alkylvinyl benzene, divinyl benzene or similar monomeric compounds and may additionally contain methacrylate or similar compounds, as well as ethylene, isobutylene, acrylonitrile or other monomers as copolymer. Compounds of this type are said to have a specific surface of at least 10 $m^2$ to 200 $m^2$ per g of resin. The resin is said to bind the substances to be separated on the outer and inner resin surface mainly through Van-der-Waals or dipole forces regardless of ionic binding or any solvation effect. The substances to be separated mentioned are organic substances with hydrophobic and hydrophilic components, e.g., surfactants, detergents, emulsifiers, dispersants, but also steroids, water-soluble enzymes, amino acids, polypeptides, proteins and hormones. The process should additionally also be suitable for separating fatty acids from aqueous solutions. It was also described that sugar solutions or solutions of other chemical substances can also be decolorized in this manner. The substances adsorbed shall be removed from the resin by heating to distillation, by treatment with steam for steam distillation, by extraction, leaching, or desorption with water, aqueous acid or alkaline solutions, or with an organic solvent which can easily be separated by fractionated distillation.

It was established according to the present invention that the substances formed as by-products during the production of citric acid by fermentation of sugar-containing raw materials, especially during the submerged fermentation of cane sugar molasses or beet sugar molasses or being present in the starting product, insofar as they cannot be separated by the above-described membrane filtration, can be bound mainly on nonionic polystyrene or polyacryl resins which are crosslinked with 2.5% vinyl benzene and which have a specific surface of ca. 300–1,000 $m^2/g$. The essentially polar citric acid is not bound in the process, so that it can be separated from the resin and from the impurities bound thereto without difficulties by subsequent washing with pure water.

The impurities in turn can be eluted completely by washing of the resin with aqueous alkali hydroxide (pH 8–13) and additional washing with a polar organic solvent, such as acetone or a lower alcohol without compromising the binding capacity of the resin, so that the resin can be recovered for further purification operations.

Even though all the above-described resins can be used, on principle, a polystyrene resin has proved to be especially favorable, which has an average particle size of ca. 30 US mesh (0.6 mm) and a minimum surface of 650 $m^2/g$ at a porosity of 1.7 mL/g. This product proved to be especially effective in different experiments; resins with similar properties, i.e., with specific surfaces of 500–800 $m^2/g$, particle sizes of 0.3–1 mm and porosities of 1–2 mL/g are therefore used with preference.

When carrying out the process true or colloidal solutions of hexacyanoferrate present in the fermentation solution are precipitated under certain circumstances by adding a small quantity of, e.g., zinc chloride or zinc sulfate, and separated by membrane filtration together with the colloidal components as well as with the higher-molecular-weight impurities. In order to achieve an economical filtration, membranes with different separation cuts are preferably used (e.g., first with a separation cut up to a molecular weight of 50,000 then to 5,000 and/or 1,000 or lower).

The fermentation solution thus subjected to a preliminary purification is then charged into a column containing a polystyrene polymer as described above until larger quantities of impurities break through, i.e., the resin is overloaded. Depending on the type of the resin the amount of solution that can be purified in this manner correponds to 5–15 times the bed volume.

Columns having lengths of about 1–10 m are suitable for the industrial process. Longer columns may also be subdivided into several shorter lengths for stability reasons and also in order to be able to perform a "quasicyclic" process ". The column may also be subdivided into several shorter lengths. Depending on the column length, the particle size and the packing density, the flow rate must be set in such a way as to achieve the best possible separation at a still acceptable throughput. Charge rates of 1–10 L solution per liter of bed volume and per hour are possible; 1.5–3 L/L and per hour have proved to be especially favorable.

The citric acid solution obtained according to this process is practically completely colorless and free from higher-molecular-weight compounds. Inorganic salts and a number of low-molecular-weight organic compounds do pass, however, through the column with the citric acid. The above-mentioned substances can be eliminated by the use of ion exchangers, and the citric acid can be crystallized to prepare the end product.

The mother liquor left after crystallization of the citric acid is reused, e.g., it is added to a new fermentation solution. This causes a further increase in yield.

However, it is also possible to precipitate the citric acid as a sparingly soluble calcium salt from the solution subjected to preliminary purification by membrane filtration and adsorption, by adding calcium salts, and to release the citric acid from the sparingly soluble calcium citrate by the addition of sulfuric acid and releasing again the citric acid from the calcium citrate. The calcium citrate which is precipitated has a substantially higher purity than according to the conventional process, so that the gypsum (calcium sulfate) obtained after the addition of sulfuric acid is whiter, on one hand, and therefore it is suitable for further processing, and the citric acid solution obtained has a higher purity, on the other hand. As a result, higher yields are obtained and a reduced number of crystallization steps is needed.

The membranes, whose throughput capacity decreases after a few hours of operation, can be cleaned simply by rinsing with e.g., a 3–5% aqueous hypochlorite solution. The separating efficiency is restored practically completely by such treatment. In order to enable a continuous operation, several membrane filter columns are preferably connected parallel in order to be able to clean some of them while the others are being used for separation.

The economy of the membrane filtration can be substantially improved by appropriate processing of the concentrates generated. For example, most of the citric acid is recovered from the concentrate by diafiltration or, after separation of the sedimentable substances, by repeated ultrafiltration, hexacyanoferrate that may be present is separated, and recycled into the production process after appropriate treatment, and the proteins present are separated and utilized in an independent fashion.

The regeneration of the polystyrene resin is of particular significance. The resin column is washed logically first with 1–2 times the bed volume of water in order to collect the citric acid still present. The first portion of washing water corresponding to one volume of bed has nearly the original citric acid concentration, and is therefore added to the main stream, and the second portion of water, corresponding to one volume of bed, which contains only little citric acid, can be used for washing in the next cycle.

The column is subsequently backwashed with a dilute a aqueous alkali, e.g., a 5% Na hydroxide solution, preferably in counterflow, using a volume corresponding to 1.5–2 times the bed volume in order to elute the majority of the material adsorbed. The residual organic substance is washed out by rinsing wtih 0.5–1 times the bed volume of acetone, whereby all impurities are removed from the column practically completely. Other solvents are less suitable. The eluents, NaOH and acetone, are displaced from the system by washing with water. The regenerated resins are thus available for a new cycle.

The solvent is recovered from the acetonic eluates by fractionated distillation. The aqueous phases are treated according to known wastewater treatment methods. Humic and fulvic acids can be isolated from the adsorber, and can be used as high-quality fertilizers.

Suitable wastewater component flows can also be incinerated.

The following examples are typical of the process or parts of it without limiting hereby the present invention. They also show that the individual purification steps can be carried out in different orders.

EXAMPLE 1

Influence of Different Adsorbent Resins

Crude, still highly contaminated citric acid solutions were charged through different Amberlite adsorbent resins and cation exchange resins in the following examples.

The said solution, containing ca. 200 mval/L citric acid and 100 mg/L synthetic fulvic acid, was passed through a column packet with 50 mL non-polar polystyrene resin Amberlite XAD-2 at room temperature and at a specfic load of 4 L/L·h after pretreatment with an Amberlite IR 120 cation exchange resin. After 60 times the bed volume of this solution had been charged the experiment was discontinued.

The resin was then regenerated with 5 times the bed volume of a 1% NaOH solution. This cycle was repeated 10 times, measuring the fulvic acid content each time by determining the COD value.

| Results: | |
|---|---|
| Cycle | % Adsorbed Fulvic acid |
| 1 | 76 |
| 2 | 78 |
| 3 | 70 |
| 4 | 74 |
| 5 | 82 |
| 6 | 79 |
| 7 | 78 |
| 8 | 76 |
| 9 | 74 |
| 10 | 73 |
| Mean value | 76 |

A solution of the same composition was passed through the adsorbent resins Amberlite XAD-4, XAD-7 and XAD-1180 under identical conditions. The following values were obtained for the retention capacity for fulvic acid.

| Cycle | XAD-4 | XAD-7 | XAD-1180 |
|---|---|---|---|
| 1 | 68 | 64 | 82 |
| 2 | 70 | 60 | 84 |
| 3 | 67 | 59 | 79 |
| 4 | 69 | 62 | 80 |
| 5 | 68 | 65 | 86 |
| 6 | 72 | 60 | 80 |
| 7 | 64 | 62 | 83 |
| Mean value | 68 | 62 | 82 |

EXAMPLE 2

Cane sugar molasses with a sugar content of 25% was passed through 50 mL Amberlite XAD-2, XAD-4, and XAD-1180 at room temperature and at a specific load of 4 L/L·h.

After passage of 7 times the bed volume the following average color uptake capacities were found:

| Type of Resin | Average Color Uptake % |
|---|---|
| XAD-2 | 64 |
| XAD-4 | 50 |
| XAD-1180 | 72 |

By washing with one bed volume of acetone 95% of the colorants adsorbed were removed. It was possible to elute 86% of the colored components with 2 bed volumes of ethanol in a comparable experiment.

EXAMPLE 3

10 L submerged fermented acid with a pH value of 2.0 to 2.2 was filtered per cycle after addition of 0.25 mg $ZnSO_4$/L fermented acid via ultrafiltration hollow fiber modules (Romicon, Inc., The Netherlands). The hollow fiber modules are self-supporting capillaries which consequently consist of membrane matrix, here of a matrix based on polysulfone. These membrane filters are suitable for separation to a molecular weight of ca. 1,000. The citric acid permeate from which the various types of impurities, such as proteins, cyanoferrates, dissolved higher-molecular-weight substances, have been removed practically completely, and the concentrate are obtained by the ultrafiltration. 8 L permeate and 2 L concentrate were obtained from 10 L acid obtained by submerged fermentation. The thickening factor was consequently 5. Analyses have revealed that ca. 75% of the organic components accompanying the citric acid were removed by this process step (the COD value is used as the evaluation parameter). The acid obtained by submerged fermentation, which was subjected to preliminary purification, was subsequently fed into an adsorber. The experimental set-up is shown in FIG. 1.

| FIG. 1 | |
| --- | --- |
| Key to the Figure: | |
| 1 | Column 1 |
| 2 | Column 2 |
| 3 | Resin bed |
| 4 | Cover material (e.g., glass wool or frit) |
| 5 | Inlet for acid obtained by submerged fermentation |
| 6 | Inlet for regenerating agent (water) |
| 7 | Connection pipe between column 1 and column 2 |
| 8 | Eluate drain pipe |
| 9 | Inlet for backwashing liquids (water, acetone, sodium hydroxide solution) |
| 10 | Drain for backwashing liquids |
| 11 | Column vent pipes |

All pipes are shown up to the first valve and the subsequent pipe sections as well as the corresponding storage tanks, pumps and receivers are omitted for simplicity's sake.

Each column was packed with 500 mL XAD-1180 (firm of Rohm & Haas Co., U.S.A.) adsorbent resin. The resin is a synthetic, insoluble polystyrene polymer, characterized by a large active surface (at least 650 $m^2/g$), nonionic nature, and by a porosity of at least 1.7 mL/g.

In the following, 500 mL resin corresponded to one volume of bed.

The data obtained in preliminary experiments have led to the following optimized mode of operation.

| Specific load | 1.5 to 3 L/L.h |
| --- | --- |
| Regeneration technique | |
| | Quantity (bed volumes) |

| | -continued |
| --- | --- |
| Column 1 | 2.0 wash water |
| | 1.5 NaOH (3.5%) |
| | 4.0 rinsing water |
| | 0.5 acetone |
| | 10.0 rinsing water |
| Column 2 | 0.5 acetone |
| | 10.0 rinsing water |

The values obtained during the loading and washing process for 4 consecutive cycles are shown in the following table.
Starting acid concentration: 1.75 val/L
Loading: 1.5 L/L·h
As was to be expected, the starting acid concentration was reached already after two volumes of fermented acid passed through the resin.

| | 1. Cycle | | 2. Cycle | | 3. Cycle | | 4. Cycle | | Φ |
| --- | --- | --- | --- | --- | --- | --- | --- | --- | --- |
| Bed Volume | Acid, vol/L | Residual Color, % | Acid, vol/L | Residual Color, % | Acid, vol/L | Residual Color, % | Acid, vol/L | Residual Color, % | Residual Color, % |
| 1 | — | 4.2 | 0.82 | 4.0 | — | 3.8 | — | 4.0 | |
| 2 | 1.72 | 9.0 | 1.70 | 9.1 | 1.70 | 8.8 | 1.70 | 9.0 | |
| 3 | 1.74 | 15.8 | 1.74 | 15.6 | 1.76 | 15.9 | 1.74 | 15.9 | 14.66 |
| 4 | 1.76 | 20.4 | 1.74 | 21.4 | 1.74 | 19.3 | 1.74 | 20.4 | |
| 5 | 1.75 | 24.4 | 1.76 | 26.4 | 1.74 | 23.4 | 1.74 | 22.4 | 24.02 |
| 6 | 1.75 | 28.6 | 1.75 | 29.8 | 1.74 | 25.4 | 1.74 | 27.4 | |
| 7 | 1.78 | 31.3 | 1.74 | 31.0 | 1.74 | 29.2 | 1.75 | 32.3 | |
| 8 | 1.74 | 34.4 | 1.74 | 36.2 | 1.74 | 32.6 | 1.75 | 33.2 | |
| 9 | 1.75 | 37.5 | 1.75 | 39.3 | 1.74 | 37.6 | 1.75 | 35.6 | |
| 10 | 1.74 | 40.2 | 1.75 | 42.1 | 1.75 | 38.5 | 1.75 | 40.0 | |

| Washing | 1,5 l/l · h | | | |
| --- | --- | --- | --- | --- |
| Bed Volume | 1. Cycle 1 Acid vol/L | 2. Cycle 2 Acid vol/L | 3. Cycle 3 Acid vol/L | 4. Cycle 4 Acid vol/L |
| 1 | 1.65 | 1.42 | 1.66 | 1.68 |
| 2 | 0.30 | — | 0.33 | 0.34 |
| 3 | — | 0.024 | 0.026 | 0.030 |
| 4 | 0.009 | 0.006 | 0.008 | 0.005 |

After regeneration of the first column with NaOH and subsequent rinsing both columns were regenerated with 0.5 bed volume each of acetone, i.e, 250 mL=196.4 g acetone, which removed ca. 95% of the residual adsorbed substances. Charge: 5 L/L·h.

The acetone was washed out with 10 bed volumes of water. The following Table shows the quantity recovered from fractions of 1 bed volume washing water in a representative cycle of column 1.

TABLE

| Wash-out of Acetone, Column 1 | |
| --- | --- |
| Acetone added | 196.4 g |
| Bed volumes of wash water | Acetone recovered (g) |
| 1. | 126.2 g |
| 2. | 18.0 g |
| 3. | 2.35 g |
| 4. | 0.85 g |
| 5. | 0.50 g |
| 6. | 0.29 g |
| 7. | 0.18 g |
| 8. | 0.14 g |
| 9. | 0.07 g |
| 10. | 0.065 g |
| Acetone recovered | 148.6 g |

This Table shows that already the first 3 bed volumes of wash water contain 98.6% of the recoverable quantity; the rest of 47.8 g is lost in the imperfectly sealed apparatus during the counterflow regeneration or during the recovery. The residual wash water, which contains only little acetone, is reused as wash water preferably in the next cycle. These losses can be avoided in a closed industrial installation, so that this experiment is not representative in this respect.

The fermented acid decolorized in adsorbent resin is passed through a strongly acidic cation exchange resin (Amberlite IR 120, Rohm & Haas Co.: sulfonated styrene/divinyl benzene copolymer with 8% DVB) and a weakly basic anion exchange resin (Amberlite IRA 68, Rohm and Haas Co.: crosslinked acrylate with dialkylamino groups) to remove inorganic salts. The resins were used in an order different from that in Examples 1 and 2.

The fermented acid thus purified is concentrated under reduced pressure until the citric acid concentration reached ca. 60 g/100 g solution, and is subjected to crystallization under reduced pressure at 30°–35° C. The citric acid crystals being formed with progressing concentration (ca. 1:7) are separated. The mother liquid is further concentrated until the enriched impurities prevent further crystallization.

The yield of three crystallization stages amounted—under laboratory conditions—to 89.8% of the theoretical value, and the crystals from the first crystallization met the specifications of the pharmacopoeia (EP [European Pharmacopoeia] Vol. III, USP 20) after a recrystallization.

The thickening factor for the ultrafiltration was 1:20 in pilot experiments with larger amounts of fermented acid.

We claim:

1. In a process for preparing highly purified citric acid from a crude citric acid fermentation solution of the type obtained by fermenting a carbohydrate-containing material to produce a fermentation mass containing citric acid in solution and filtering the fermentation mass to produce a crude citric acid fermentation solution, the improvement comprising (a) separating higher molecular weight impurities above about 1,000 mw from the citric acid fermentation solution by membrane ultrafiltration; (b) passing the membrane-filtered citric acid solution over a non-ionic adsorbent resin having a specific surface of 300–1,000 $m^2/g$ to remove non-ionic impurities having a molecular weight below about 1,000 mw from the solution; (c) separating cationic and anionic impurities from the citric acid solution by passing the eluate from the non-ionic adsorbent resin over a cation exchange resin and an anion exchange resin; and (d) concentrating and recovering highly purified citric acid.

2. The process of claim 1 wherein the citric acid is recovered in step (d) by adding a calcium salt to the concentrated purified citric acid solution to precipitate insoluble calcium citrate, adding sulfuric acid to the solid calcium citrate, and recovering citric acid.

3. The process of claim 2 wherein following the addition of sulfuric acid, calcium sulfate is also recovered.

4. The process of claim 3 wherein the calcium salt added to precipitate calcium citrate is recycled calcium sulfate recovered from the calcium citrate acidification.

5. The process of claim 1 wherein impurities bound to the adsorbent resin are eluted (a) with aqueous alkali hydroxide with pH 8–13, and (b) with a polar organic solvent comprising acetone or a lower alcohol, to regenerate the resin for reuse according to claim 1.

6. The process of claim 1 wherein hexacyanoferrate, protein- or amino acid impurities are removed in the membrane filtration step (a) and humic acid and fulvic acid impurities are removed in the adsorption step (b).

7. The process of claim 1 wherein the cation and anion exchange resins are regenerated and reused.

8. The process of claim 1 wherein the solution left after the recovery of the citric acid in step (d) is recycled to the starting citric acid fermentation solution.

9. The process of claim 1 wherein the non-ionic adsorbent resin is polystyrene or polyacrylate.

10. The process of claim 1 wherein the citric acid recovered in step (d) is USP grade citric acid.

11. The process of claim 1 wherein the non-ionic adsorbent resin is a vinyl benzene cross-linked polystyrene or polyacrylate resin.

12. The process of claim 1 wherein the non-ionic adsorbent resin has a specific surface of about 500 to 800 $m^2/g$.

13. The process of claim 1 wherein the cation exchange resin in step (c) is a strongly acidic cation exchange resin and the anionic exchange resin is a weakly basic anionic exchange resin.

14. The process of claim 1 wherein the solution is passed first through the cationic exchange resin and second through the anionic exchange resin.

15. The process of claim 1 wherein steps (b) and (c) are carried out in a continuous cycling process through columns containing the resins.

16. The process of claim 1 wherein any hexacyanoferrate impurities present in the citric acid solution are removed in step (a) after pre-treatment of the citric acid fermentation solution by addition of a soluble zinc salt to the citric acid solution before membrane filtration to coagulate or precipitate the hexacyanoferrate impurities.

17. The process of claim 1 wherein the carbohydrate-containing material comprises cane sugar molasses.

18. The process of claim 1 wherein the higher molecular-weight impurities separated in step (a) include proteins.

19. The process of claim 1 wherein the higher molecular weight impurities have a molecular weight between about 1,000 and 50,000.

20. The process of claim 1 wherein the organic solvent is recovered from the eluate by fractional distillation.

21. The process of claim 1 wherein the cation and anion exchange resins are regenerated and reused.

22. The process of claim 1 wherein the ultrafiltration is carried out with hollow fiber modules.

23. The process of claim 12 wherein the non-ionic absorbent resin has a porosity of 1 to 2 mL/g.

24. The process of claim 15 wherein the columns are connected in parallel.

* * * * *